United States Patent [19]

Kim

[11] Patent Number: 4,849,420
[45] Date of Patent: Jul. 18, 1989

[54] 2,3,11,12-SUBSTITUTED-5,6,8,9,14,14A-HEXAHYDROISOQUINO-[1,2-B][3]BENZAZEPINES

[75] Inventor: Dong H. Kim, Pohang, D.P.R. of Korea

[73] Assignee: American Home Products Corporation, New York, N.Y.

[21] Appl. No.: 148,471

[22] Filed: Jan. 26, 1988

[51] Int. Cl.⁴ .................. A61K 31/55; C07D 471/04
[52] U.S. Cl. ................................. 514/214; 540/576
[58] Field of Search .................... 540/576; 514/214

[56]  References Cited
U.S. PATENT DOCUMENTS
3,383,388  5/1968  Houlihan et al. ................ 540/576

OTHER PUBLICATIONS
Hocquemiller et al., Journal of Natural Products, 47, 539–540 (1984).
Cave et al., Planta Medica, 50, 517–519 (1984).

Primary Examiner—Mary C. Lee
Assistant Examiner—MarySue Howard
Attorney, Agent, or Firm—Arthur G. Seifert

[57] ABSTRACT

This disclosure concerns antihypertensive isoquinobenzazepines of the formula

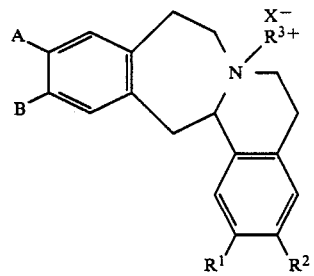

wherein
A and B may be, independently, hydrogen, hydroxy or $C_1$–$C_6$ alkoxy, or A and B together may be —O—$(CH_2)_n$—O— wherein n may be 1,2 or 3;
$R^1$ and $R^2$ may be, independently, hydrogen, hydroxy or $C_1$–$C_6$ alkoxy;
$R^3$ may be hydrogen or $C_1$–$C_4$; and
X may be chlorine, bromine or iodine.

34 Claims, No Drawings

2,3,11,12-SUBSTITUTED-5,6,8,9,14,14A-HEXAHYDROISOQUINO-[1,2-B][3]BENZAZEPINES

This invention concerns 2,3,11,12-substituted-5,6,8,9,14,14a-hexahydroisoquino[1,2-b][3]benzazepines of the formula:

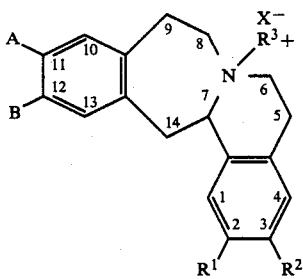

XV wherein
A and B may be, independently, hydrogen, hydroxy or $C_1$-$C_6$ alkoxy, or A and B together may be —O—$(CH_2)_n$—O— wherein n may be 1, 2 or 3;
$R^1$ and $R^2$ may be, independently, hydrogen, hydroxy or $C_1$-$C_6$ alkoxy;
$R^3$ may be hydrogen or $C_1$-$C_4$ alkyl; and
X may be chlorine, bromine or iodine.

The compounds of formula XV are antihypertensive agents or intermediates for such anti-hypertensive agents. The invention also includes other novel intermediates and processes for the production of compounds of formula XV or intermediates therefore.

BACKGROUND OF THE INVENTION

Saulatine and dehydrosaulatine, pictured below, were recently isolated by Hocquemiller et al. (Journal of Natural Products, 47, 539 (1984)) from *Abuta bullata* Moldenke.

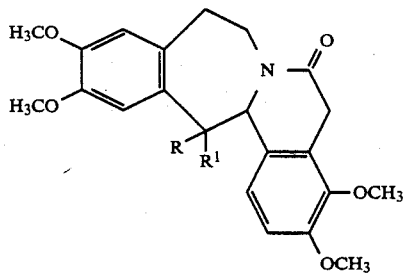

Saulatine: R, $R^1$ = O
Hydrosaulatine: R = H, $R^1$ = OH

These molecules differ from Applicant's claimed molecules in having the oxo substituent adjacent the isoquinoline nitrogen ring atom (i.e. in the 6 position), an oxo or hydroxy substituent in the benzodiazepine ring (i.e. at the 14 position), and a methoxy substituent at the 4 position.

A further related natural product is N-methylisocorypalmine whose structure is

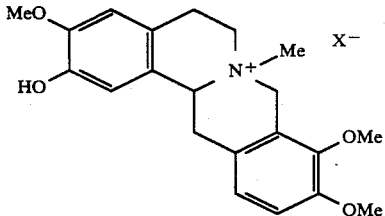

N—Methylisocorypalmine

N-methylisocorypalmine was isolated by Cave et al., Planta Medica, 50, 517 (1984), from *Cymbopetalum brasiliense* Benth and stated to be partly responsible for the positive ionotropic activity of the extract from which it was isolated. This molecule differs from Applicant's claimed molecules in having a perhydrohexine ring where Applicants' have a perhydroazepine ring, in the points of attachment of the isoquinoline ring to this ring, and in having a methoxy group in the 5-position.

DETAILED DESCRIPTION OF THE INVENTION

Preferred compounds of the invention are, independently, those in which one or both of $R^1$ and $R^2$ is methoxy, ethoxy, or propoxy; $R^3$ is methyl or ethyl; and n is 1 (ie. —O—$(CH_2)_n$—O— is —O—$CH_2$—O—).

Most preferred compounds of formula XV are those in which one of $R^1$ and $R^2$ is hydroxy, the other is hydrogen and A and B are both hydroxy. A preferred group of compounds of formula XV are those wherein $R^1$, $R^2$, A and B are each hydroxy; one of $R^1$ and $R^2$ is methoxy, the other is hydrogen, and A and B form a 1,3-dioxolo group (n is 1); and $R^1$ and $R^2$ are each methoxy, A and B form a 1,3-dioxolo group (n is 1), $R^3$ is methyl, and X is iodine. The most preferred compound of the invention of formula XV is the compound of Example 23. Further preferred compounds of the invention of formula XV are the compounds of Examples 24, 22, 20 and 19.

The following two reaction schemes depict the novel process for producing the compounds of the invention of formula XV.

Scheme I

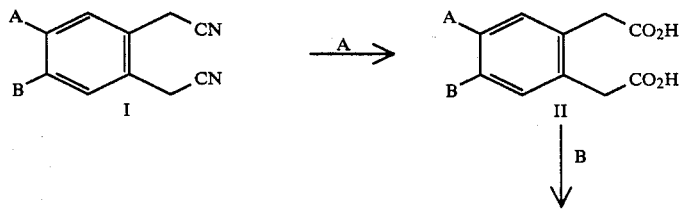

Scheme I
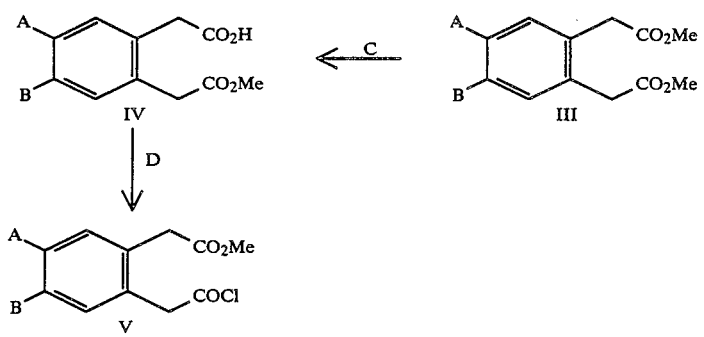
Scheme II
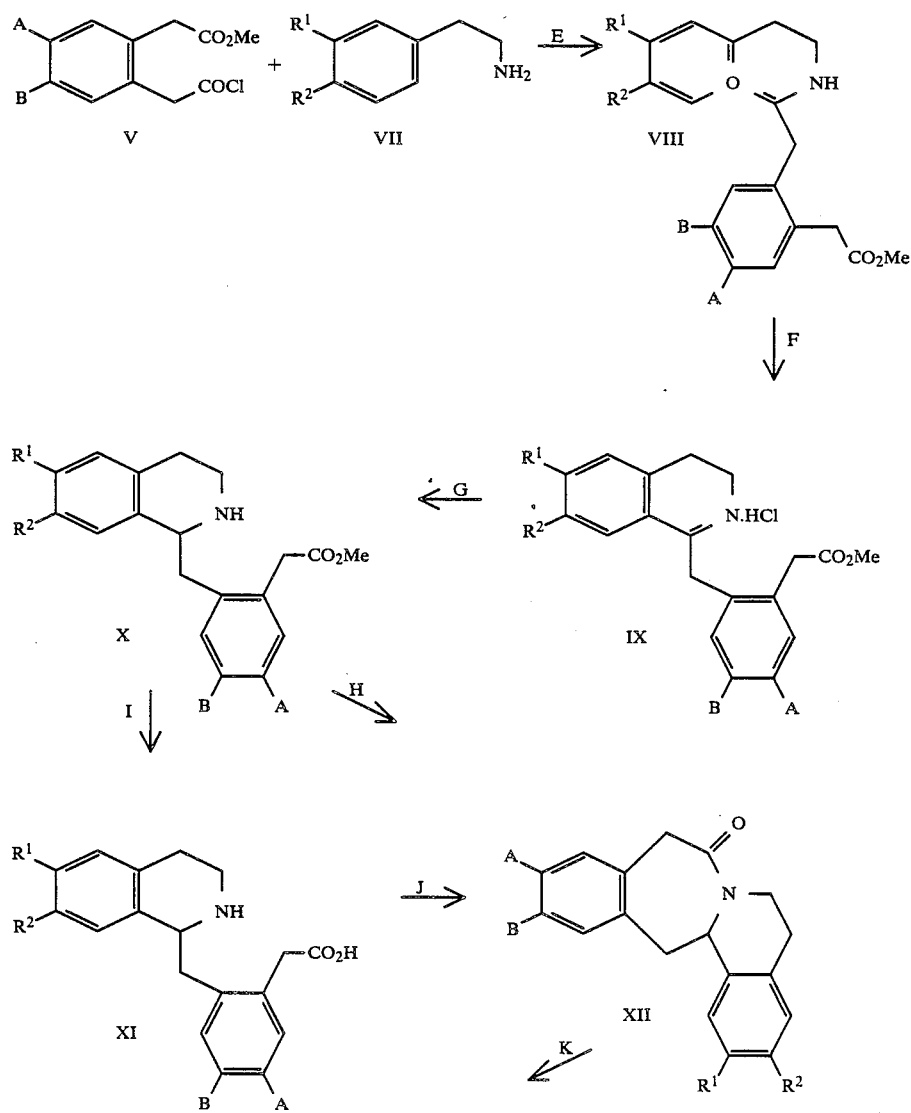

Scheme II
-continued

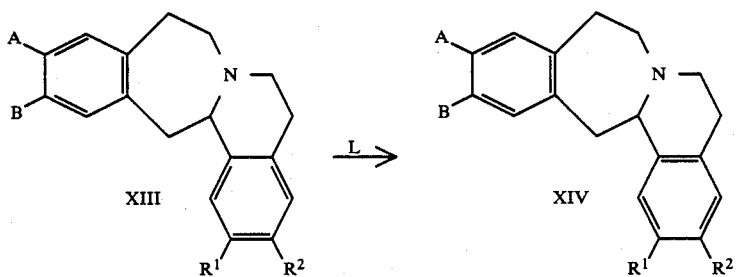

In Scheme I, Step A, the conversion of the diacetonitrile I to the diacetic acid II is carried out in a conventional manner as shown in Example 1. The conversion is made therein using potassium hydroxide in ethylene glycol monoethyl ether at reflux temperatures for seven hours. Step B comprises the esterification of the diacetic acid II to the dimethyl ester thereof, also in a conventional manner. This step is shown in Example 2 where methanol was saturated with HCl gas (at 0° C.) and allowed to react overnight at 45° C. In Step C, one of the esters is converted back to an acid. This conversion is carried out in a conventional manner as shown in Example 3. There, the diacetic acid, dimethyl ester III is dissolved in methanol, to which sodium hydroxide is added over a one hour period. Anhydrous ether is then added and the resulting solution is stirred at room temperature for 20 hours. In Step D of Scheme 1, the monoacetic acid moiety is converted to its acid chloride in a conventional manner. This step is illustrated in the first reaction of examples 4, 5 and 6, respectively. Thionyl chloride is used here as the chlorinating agent. The starting material of Example 1 (Step A), namely, 1,3-benzodioxale-5,6-diacetonitrile (A+B=OCH$_2$O) was prepared as described by B. Pecherer et al., Journal of Heterocyclic Chemistry, 9, 617 (1972) from 5,6-dichloromethyl-1,3-benzodioxole. The latter compound was reported by F. Dollacher et al., Ann. Chem., 643, 67 (1981). Where A and B are both hydrogen, Step A may be eliminated since 1,2-benzenediacetic acid (II) is commercially available.

In Scheme II, Step E, the monoacetic acid, acid chloride moiety of V (Step D) is condensed with the amine moiety of the phenethylamine VII. The condensation of the acid chloride V and the amine VII is carried out in a conventional manner in the presence of an acid scavenger such as triethylamine. Step E comprises the second reaction of Examples 4, 5 and 6, respectively, where the condensed products VIIIa, VIIIb, and VIIIc, respectively, are obtained. Step F comprises the first ring closure, in which the 3,4-dihydroisoquinoline ring is formed. In step F, the condensation agent for producing the first ring closure may be phosphorus oxychloride. The reaction may be conveniently carried out as in Examples 7, 8 and 9 where toluene is used as an inert solvent and the ring condensation is carried out at reflux temperatures for about 30 minutes. The 2-[(3,4-dihydro-6,7-substituted-1-isoquinolyl)methyl]-3,4-substituted-benzeneacetic acid, 5-alkyl esters IXa, IXb and IXc are recovered, respectively, in Examples 7, 8 and 9.

In Scheme II, Step G, the 3,4-dihydroisoquinoline IX is hydrogenated to produce the corresponding 1,2,3,4-tetrahydroisoquinoline X. Aqueous sodium borohydride is used as the hydrogenating agent. Methanol and water are conveniently used as a solvent. After combining the 3,4-dihydroisoquinoline IX and aqueous sodium borohydride in the methanol/water solution under chilling in ice, the ice is removed and the reaction is allowed to proceed at room temperature under vigorous stirring for about 45 minutes. The resulting 2-[(1,2,3,4-tetrahydro-6,7-substituted-1-isoquinolyl)methyl]-3,4-substituted-benzeneacetic acid, alkyl esters Xa, Xb, and Xc are obtained, respectively, in Examples 10, 11 and 12.

In Step G, the second ring closure, forming the benzepin-8(6H)-one ring, is made by condensing the acetic acid ester moiety with the isoquinoline ring nitrogen. This condensation may be carried out as in Examples 13, 14 and 15 by treating the 2-[(1,2,3,4-tetrahydro-6,7-substituted-1-isoquinolyl)methyl]-3,4-substituted-benzeneacetic acid, alkyl esters Xa, Xb and Xc, respectively, with sodium carbonate in methanol under heating at reflux temperatures for 3.5 hours. The resulting 5,9,15,15a-tetrahydro-2,3-substituted-11,12-substituted-isoquino[1,2-b][3]benzazepin-8(6H)-ones XIIa, XIIb, and XIIc are recovered in Examples 13, 14 and 15, respectively. Alternately, Steps I and J may yield the isoquino[1,2-b][3]benzazepin-8(6H)-ones XII. These steps are shown in Examples 16 and 17, where the products corresponding to XIc and XIIc are obtained.

In Step K the oxo group on the azepine ring is reduced using borane-tetrahydrofuran complex in tetrahydrofuran. The reactants are admixed under ice-chilling for about 30 minutes, and the reaction is continued under heating at reflux temperatures for about 1 hour. This reduction Step K is illustrated in Examples 18, 19 and 20, where the resulting 5,6,8,9,15,15a-hexahydro-2,3-substituted-11,12-substituted-isoquino[1,2-b][3]benzazepines XIIIa, XIIIb and XIIIc, respectively, are recovered. It will be appreciated that some of the compounds of formula XIII represent desired final, pharmacologically active compounds of formula XV. Other compounds of formula XIII are intermediates for final, pharmacologically active compounds of formula XIV and, as such, are also included in the compounds of formula XV.

Step L is required to hydrolyze the compounds of formula XIII in which A+B or R$^1$+R$^2$ are O—(CH$_2$)$_n$—O to hydroxy or alkoxy moieties, or to convert A, B, R$^1$ and/or R$^2$=alkoxy to a hydroxy moiety. Step L is also utilized to convert the claimed compounds of formulas XIII or XIV into the N-alkyl halides of formulas XIV and XV. Example 21 illustrates the conversion of a 2,3-dimethoxy compound of formula XIII (XIIIc, Ex. 20) to the corresponding 2,3-diol of formulas XIV and XV. This hydrolysis is accomplished using hydrobromic acid and glacial acetic acid with heating under reflux for 2.5 hours. Example 22 illustrates the conversion of the 2,3-methoxy-11,12-dioxolo compound of formula XIII (XIIIa, Ex. 18) to the corresponding 2,3,11,12-tetrol of formulas XIV and XV. This hydrolysis was accomplished using first boron tribromide in methylene chloride with stirring overnight at room temperature. The resulting solution was treated by adding methanol dropwise and then evaporating to a solid residue. The residue was treated with 5 percent aqueous sodium bicarbonate, and further work-up yielded the desired tetrol. Example 23 illustrates the conversion of 5,6,8,9,15,15a-hexahydro-3-methoxy[1,3]dioxolo[4,5-h]isoquino[1,2-b][3]benzazepine of Formula XIII (XIIIb, Ex. 19) to the corresponding 3,11,12-triol of formulas XIV and XV. This hydrolysis was accomplished, as in Example 22, first utilizing boron tribromide. However, the resulting product was extracted with ethyl acetate, evaporated to a solid and the solid dissolved in hot ethanol. This solution was then treated with an ethanolic hydrogen chloride solution. Further work-up yielded the desired triol of formulas XIV and XV. Finally, Example 24 illustrates the conversion of a compound of Formula XIII (XIIIa, Ex. 18) to the corresponding 7-methyl iodide of formulas XIV and XV. This quaternization of the ring nitrogen is accomplished by treatment of the compound of formula XIII with methyl iodide in dimethylformamide at room temperature in a nitrogen atmosphere for 2 days.

The ability of the compounds of the invention to reduce high blood pressure is determined by a standard pharmacological procedure utilizing conscious, spontaneously hypertensive rats (SHR) as subjects. This procedure is performed in the following manner.

Systolic blood pressure of male SHR (Taconic Farms) is measured by indirect tail plethysmography using a system designed and built by Narco Bio-Systems-(Model MK-IV). Groups consisting of 4 rats receive a single oral dose of the test compound. Rats are warmed in a heated chamber at 38° C. for 10 min. prior to measurement of systolic pressure to increase the accuracy of the measurements. Systolic blood pressures and heart rates are read prior to drug administration and at 1.5, 4 and 24 hours thereafter. Systolic pressure and heart rate data are collected in an Hewlett Packard 88 computer. Data are grouped and summarized, with the mean change in pressure and heart rate at each time period calculated. Data card are printed for each compound tested. These cards include compound name, dose tested, individual rat I.D., control systolic pressure and heart rate and change in both parameter for each rat, and the group mean values for each measurement. The results are recorded and summarized according to the following categories of activity:

| Activity | number | −mm Hg |
| --- | --- | --- |
| not significant | 0 | 0–15 |
| borderline | 1 | 16–25 |
| slight | 2 | 26–35 |
| moderate | 3 | 36–50 |
| marked | 4 | >50 |

When measured according to this procedure the standard compound phentolamine at a dose of 5 mg/kg reduces systolic blood pressure at 1.5 hours after administration by 71 mm of Hg. The standard compound hydralazine at a dose of 1 mg/kg reduces systolic blood pressure 1.5 hours after administration by 55 mm of Hg.

When tested according to this procedure the compounds of the invention showed activity as follows:

| Compound Example No. Formula | Dose Mg/kg | Time hrs. | Activity |
| --- | --- | --- | --- |
| 7 (IXa) | 50 | 1.5 | borderline |
| 10 (Xa) | 25 | 1.5 | slight |
|  | 25 | 4.0 | slight |
| 14 (XIIb) | 25 | 4.0 | borderline |
| 19 (XIIIb) | 25 | 1.5 | slight |
|  | 25 | 4.0 | borderline |
| 20 (XIIIb) | 50 | 1.5 | borderline |
| 22 (XIVa) | 25 | 1.5 | borderline |
| 23 (XIVb) | 25 | 1.5 | marked |
|  | 25 | 4.0 | marked |
|  | 10 | 1.5 | moderate |
|  | 10 | 4.0 | moderate |
| 24 (XIVa) | 25 | 1.5 | moderate |
|  | 10 | 1.5 | borderline |
|  | 10 | 4.0 | borderline |

In addition to the hydrohalide and alkylhalide salts ($R^3X$) included in formula XV, the compounds of formulas XIII, XIV and XV, and other intermediate compounds therefore, may exist as acid addition salts of other inorganic or organic cations and anions. Pharmaceutically acceptable acid addition salts are preferred, examples of which are hydrochloride, hydrobromide, hydroiodide, sulphate, nitrate, phosphate, sulphonate (such as methanesulfonate and p-toluenesulphonate), acetate, maleate, citrate, fumarate, tartrate, malonate and formate salts. Other salts may be used to isolate or recover intermediate compounds. Such salts may be converted to the free base and/or interconverted to other salts in a known manner.

In another aspect, this invention includes a method of treating hypertension which comprises administering to a mammal, including man, in need thereof an amount of a compound of formula XIII, XIV or XV, or a pharmaceutically acceptable salt thereof, effective to reduce the blood pressure of such mammal. Excluded from this method of treatment aspect of the invention are the compounds of formulas XIII and XV in which $R^1 + R^2 = -O(CH_2)_nO-$ and A and B are each methoxy and $R^3$ is hydrogen. Also excluded from the method of treatment aspect of the invention are the compounds of XIV and XV in which $R^1$, $R^2$ and $R^3$ are hydrogen and X and Y are hydroxy. An especially preferred compound for the method of treatment aspect of the invention is the compound of Example 23. A particularly preferred compound for the method of treatment aspect of the invention is the compound of Example 24. Other preferred compounds for the method of treatment aspect of the invention are the compounds of Examples 19, 20 and 22.

When used to treat hypertension the compounds may be used alone or in combination with a suitable pharmaceutically acceptable carrier. Another aspect of the invention includes a pharmaceutical composition for treating hypertension comprising an amount of a compound of formula XIII, XIV, or XV effective to treat hypertension in a mammal, including man, in combination with a pharmaceutically acceptable carrier. Excluded and preferred compounds for this aspect of the invention are the same as those for the method of treatment aspect of the invention.

When used to treat hypertension the compounds of the invention, in combination with a pharmaceutically acceptable carrier as required or desired, may be administered orally or parenterally. Oral administration is preferred. Intravenous and subcutaneous administration are preferred examples of parenteral administration.

The following examples illustrate the processes for producing the various pharmacologically active or intermediate compounds of the invention.

EXAMPLE 1

1,2-Benzodioxole-5,6-diacetic acid

Potassium hydroxide pellets (87%) (64.57 g, 1 mole) were dissolved in ethylene glycol monomethyl ether (300 ml). To this solution was added 1,3-benzodioxole-5,6-diacetonitrile (I) (40.04, 0.2 mole), and the resulting mixture was heated under reflux for 7 hours. The reaction mixture was cooled to room temperature, and ether (320 ml) was added. The resulting mixture was chilled in ice, and a precipitate was collected on a filter and washed with ethanol repeatedly until a colorless washing was obtained. The filter residue was dissolved in hot water (150 ml), and the solution was filtered. Acidification of the filtrate with dilute HCl followed by chilling in ice caused separation of a precipitate which was collected on a filter and washed with water several times to give the product (10.16 g, 21%), mp 206°–208° dec.

Analysis: $C_{11}H_{10}O_6$ Calculated: C, 55.46; H, 4.23 Found: C, 55.53; H, 4.22

EXAMPLE 2

1,3-Benzodioxole-5,6-diacetic acid dimethyl ester (III)

A mixture of 1,3-benzodioxole-5,6-acetic acid (II) (16.66 g, 0.07 mole) and methanol (167 ml) was saturated with HCl gas at 0°, and the resulting solution was stirred at 45° overnight, then concentrated on a steam bath to a precipitate which was collected on a filter and washed with methanol to give 16.9 g (91%) of the product, mp 79°–82°. An analytical sample was obtained by recrystallization from methanol melted at 81°–83°.

Analysis: $CH_{13}H_{14}O_6$ Calculated: C, 58.64; H, 5.30 Found: C, 58.55; H, 5.30

EXAMPLE 3

1,3-Benzodioxolo-5,6-diacetic acid 5-methyl ester (IVa)

Sodium hydroxide solution (1.0N, 526 ml, 52.6 mmole) was added over the period of 1 hour with vigorous stirring to a solution of 1,3-benzodioxole-5,6-diacetic acid dimethyl ester (III) (15.5 g, 52.6 mmole) and methanol (700 ml). Anhydrous ether (250 ml) was added. The resulting mixture was stirred at room temperature for 20 hours, then chilled in ice. The precipitate that separated was filtered and the filter esidue was washed with methanol. The combined filtrate and washings were evaporated on a rotary evaporator to give a gummy residue which was dissolved in a mixture of water (70 ml) and ether (70 ml). The aqueous layer was collected, and wahed with ether two additional times, then acidified with dilute HCl. Chilling of the acidic solution in ice caused separation of a precipitate which was collected on a filter and washed with water to give 10.9 g (76%) of the title product, mp 105°–107°.

Analysis: $C_{12}H_{17}O_6$ Calculated: C, 57.14; H, 4.80 Found: C, 56.83; H, 4.72

The filter residue that was obtained from the reaction mixture was dissolved in a small amount of water, and acidified with dilute HCl to cause separation of a precipitate. The mixture was chilled in ice, and the precipitate was collected on a filter and wahed with water to give 1.3 g of 1,3-benzodioxole-5,6-diacetic acid.

The combined ether washings were washed with brine, and concentrated on a steam bath, then chilled in ice to cause separation of 1.95 g of the unreacted starting material.

EXAMPLE 4

6-[2-[[2-(3,4-Dimethoxyphenyl)ethyl]amino]-2-oxoethyl]-1,3-benzodioxole-5-acetic acid methyl ester (VIIIa)

To a mixture of 1,3-benzodioxolo-5,6-diacetic acid 5-methyl ester (IVa) (17.65 g, 0.07 mole), anhydrous ether (700 ml) and thionyl chloride (9.16 g, 0.077 mole) was added 3 drops of triethylamine. The resulting mixture was stirred at room temperature overnight, then heated under reflux fr 2 hours. The reaction mixture was cooled to room temperature, and filtered. The filtrate was evaporated on a rotary evaporator to give an oily residue. The residue was coevaporated with anhydrous ether several times, then placed in vacuo to give the corresponding acid chloride. The latter acid chloride (Va) was dissolved in methylene chloride (50 ml), and was added to a stirred ice-chilled mixture of 3,4-dimethoxyphenethylamine (VIIa) (12.69 g, 0.07 mole), triethylamine (7.07 g, 0.07 mole), and methylene chloride (300 ml). The resulting mixture was stirred at room temperature for 2 hours, washed with water, dried (sodium sulfate), and evaporated on a rotary evaporator to give a solid residue. Recrystallization of the crude product from methanol afforded 27 g (93%) of the product, mp 122°–125°. The analytical sample that was recrystalized from methanol melted at 124°–126°.

Analysis: $C_{22}H_{25}NO_7$ Calculated: C, 63.60; H, 6.07; N, 3.37 Found: C, 63.21, H, 5.86; N, 3.43

EXAMPLE 5

6-[2[[2-(3-Methoxyphenyl)ethyl]amino]-2-oxoethyl]-1,3-benzodioxole-5-acetic acid methyl ester (VIIIb)

The title compound was prepared as described in Example 4. 1,3-Benzodioxolo-5,6-diazolo-5,6-diacetic acid 5-methyl ester (17.655 g, 0.07 mole) was converted into the corresponding acid chloride by the treatment with thionyl chloride (9.163 g, 0.077 mole). The acid chloride (Vb) that was obtained was then allowed to react with 3-methoxyphenethylamine (VIIb) (10.58 g, 0.07 mole) in the presence of triethylamine (7.07 g, 0.07 mole) in methylene chloride. The product that was obtained initially as an oil solidified on standing. Recrystallization from methanol afforded 18.9 g (70%) of the titled product, mp 81°–83°.

Analysis: $C_{21}H_{23}NO_6$ Calculated: C, 65.44; H, 6.01; N, 3.63 Found: C, 65.63; H, 6.03; N, 3.58

EXAMPLE 6

2-[2-[[2-(3,4-Dimethoxyphenyl)ethyl]amino]-2-oxoethyl]benzeneacetic acid methyl ester (VIIIc)

Thionyl chloride (4.0 g, 0.0336 mole) was added dropwise to a solution obtained by dissolving 1,2-benzenediacetic acid 1-methyl ester (IVa) (6.25 g, 0.03 mole) in anhydrous ether (250 ml). The resulting mixture was stirred at room temperature overnight, then evaporated on a rotary evaporator to give an oily residue. The residue was dissolved in anhydrous ether, and the solution was evaporated on a rotary evaporator. This dissolution in ether and evaporation on a rotary evaporator was repeated two additional times. The residue was kept in vacuo for several hours, then was dissolved in methylene chloride (20 ml). The solution was added dropwise to a well stirred and ice-chilled methylene chloride solution of 2-(3,4-dimethoxyphenyl)ethylamine (VIIc) (5.43 g, 0.03 mole) and triethylamine (3.03 g, 0.03 mole) in methylene chloride (100 ml). The chilling source was removed, and the stirring was continued for 2 hours. The reaction mixture was washed with water twice, then with brine and dried over anhydrous sodium sulfate. Evaporation of methlene chloride on a rotary evaporator gave a thick oil which solidified upon chilling with scratching. The crude product was dissolved in anhydrous ether (800 ml) with warming on a steam bath, and filtered to remove an insoluble material. The filtrate was concentrated on a rotary evaporator to about 150 ml, and chilled in ice to cause separation of a precipitate. The precipitate was colleced on a filter to give the titled produce (3.3 g, 30%), mp 88°–91°: an analytical sample recrystallized from ether melted at 92°–94°.

Analysis: $C_{21}H_{25}NO_5$ Calculated: C, 67.90; H, 6.78; N, 3.77 Found: C, 67.82; H, 6.66; N, 3.66

EXAMPLE 7

6-[(3,4-Dihydro-6,7-dimethoxy-1-isoquinolinyl)methyl]-1,3-benzodiozole-5-acetic acid methyl ester (IXa)

Four grams (0.01 mole) of 6-[2-[[2-(3,4-dimethoxyphenyl)ethI]amino]-2-oxoethyl]-1,3-benzodioxole-5-acetic acid methyl ester (VIIIa) was dissolved in warm toluene which had been dried using a Dean-Stark trap. Phosphorus oxychloride (3.383 g, 0.025 mole) was added to the toluene solution, and the reaction mixture was heated under reflux for 30 minutes, then chilled in ice with addition of anhydrous ether (120 ml). A precipitate was collected on a filter, wahed with acetone, and recrystallized from a mixture of methanol and acetone to give the titled product (2.76 g, 62%), mp 191°–193° dec. The analytical sample that was obtained by recrystallization from methanol and acetone melted at 194°–196° dec.

Analysis: $C_{22}H_{23}NO_6HCl.HCl.0.5H_2O$ Calculated: C, 59.66; H, 5.69; N, 3.16 Found: C, 59.57; H, 5.71; N, 3.17

EXAMPLE 8

6-[(3,4-Dihydro-6-methoxy-1-isoquinolinyl)methyl]-1,3-benzdioxole-5-acetic acid methyl ester (IXb)

The title compound was prepared as described in Example 7 using 6-[2-[[2-(3-methoxyphenyl)ethyl]amino]-2-oxoethyl]-1,3-benzodioxole-5-acetic acid methyl ester (VIIIb) (7.71 g, 0.02 mole) and phosphorus oxychloride (7.66 g, 0.05 mole). The crystalline product that was obtained was recrystallized from acetonitrile. The product was amounted to 1.4 g (15%), and melted at 182°–184° dec.

Analysis: $C_{21}H_{21}NO_5.H_3PO_4.\frac{1}{2}H_2O$ Calculated: C, 53.16; H, 5.31; N, 2.95 Found: C, 53.17; H, 5.08; N, 3.09

EXAMPLE 9

2-[(3,4-Dihydro-6,7-dimethoxy-1-esoquinolyl)methyl]-benzeneacetic acid methyl ester (IXc)

The title compound was prepared as described in Example 7 by allowing 2-[2-[[2-(3,4-dimethoxyphenyl)ethyl]amino]-2-oxoethyl]benzeneacetic acid methyl ester (VIIIc) (3.0 g, 8 mmole) to react with phosphorus oxychloride (1.53 g, 10 mmole) in boiling toluene. A crude product was purified by recrystallization from ethanol to give the titled product (1.8 g, 50) as the phosphoric acid salt, mp 108°–110°, Mass spec (CI) m/z 354 (M+H); (EI) m/z 353, 280.

Analysis: $C_{21}H_{23}NO_4.H_3PO_4$ Calculated: C, 55.87; H, 5.80; N, 3.10 Found: C, 55.75; H, 5.78; N, 3.11

EXAMPLE 10

6-[(1,2,3,4-Tetrahydro-6,7-dimethoxy-1-isoquinolinyl)methyl]-1,3-benzodioxole-5-acetic acid methyl ester (Xa)

Six and one-half grams (14 mmole) of 6-[(3,4-dihydro-6,7-dimethoxy-1-isoquinolinyl)methyl]-1,3-benzodioxole-5-acetic acid methyl ester hydrochloride (IXa, Ex. 7) was dissolved in methanol (40 ml) and water (120 ml), and the solution was chilled in ice. Aqueous sodium borohydride obtained by dissolving 1.0 g of sodium borohydride in 20 ml of water was added dropwise with vigorous stirring. The resulting mixture was allowed to sit at room temperature with occasional hand swirling for 45 minutes. About 100 ml of ether was added, and the mixture was stirred vigorously, and the ether layer was collected. The aqueous layer was made alkaline by addition of dilute sodium hydroxide wolution and extracted with ether twice. The combined ether extracts were washed with brine, dried ($Na_2SO_4$), then evaporated on a rotary evaporator to give an oily residue which solidified on standing to give the titled product (4.0 g, 68%). Recrystallization from ether afforded an analytical sample, mp 99°–101°.

Analysis: $C_{22}H_{26}NO_6$ Calculated: C, 65.98; H, 6.55; N, 3.50 Found: C, 66.17; H, 6.28; N, 3.53

EXAMPLE 11

6-[(1,2,3,4-Tetrahydro-6-methoxy-1-isoquinolinyl)methyl]-1,3-benzodioxole-5-acetic acid methyl ester (Xb)

The title compound ws prepared as described in Example 10 by reducing 6-[(3,4-dihydro-6-methoxy-1-isoquinolinyl)methyl]-1,3-benzodioxole-5-acetic acid methyl ester (IXb, Ex. 8) with sodium borohydride. The resinous product that was obtained was used in the subsequent reaction without purification.

EXAMPLE 12

2-[(1,2,3,4-Tetrahydro-6,7-dimethoxy-1-isoquinolyl)methyl]benzene-acetic acid methyl ester (Xc)

The title compound was prepared was described in Example 10 from 2-[(3,4-dihydro-6,7-dimethoxy-1-isoquinolyl)methyl]benzeneacetic acid methyl ester (IXc, Ex. 9) and sodium borohydride, and the oil product was usd in the subsequent reaction without purification.

EXAMPLE 13

5,9,15,15a-Tetrahydro-2,3-dimethoxy[1,3]dioxolo[4,5-h]isoquino[1,2-b][3]benzazepin-8(6H)-one (XIIa)

A mixture of 6-[1,2,3,4-tetrahydro-6,7-dimethoxy-1-isoquinolinyl)methyl]-1,3-benzodioxole-5-acetic acid methyl ester (Xa, Ex. 10) (8.0 g, 0.02 mole), sodium carbonate (1.6 g, 0.015 mle) and methanol (210 ml) was heated under reflux for 3.5 hours. Addition of water (100 ml) and chilling in ice caused separation of a precipitate which as collected on a filter and washed with water to give the titled product (7.03 g, 96%), mp 207°–209°. Recrystallization from ethanol gave an analytical sample, mp 208°–210°.

Analysis: $C_{21}H_{21}NO_5$: Calculated: C, 68.65; H, 5.76; N, 3.81  Found: C, 68.62 H, 5.77; N, 3.84

EXAMPLE 14

5,9,15,15a-Tetrahydro-3-methoxy-[1,3]dioxolo[4,5-h]isoquino[1,2-b][3]benzazepin-8(6H)-one XIIb)

The title compound ws prepared as described in Example 13 by treating 6-[1,2,3,4-tetrahydro-6-methoxy-1-isoquinolinyl)methyl]-1,3-benzodioxole-5-acetic acid methyl ester (Xb, Ex. 11) with sodium carbonate in methanol. The crude product (mp 154°–156°) obtained in 81.5% yield was recrystallized from ethanol, mp 154°–156°. Mass spec (CI) m/z 338 (M+H).

Analysis: $C_{20}H_{19}NO_4 \cdot \frac{1}{2}EtOH$ Calculated: C, 69.98; H, 6.15; N, 3.89  Found: C, 69.61; H, 5.80; N, 3.91

EXAMPLE 15

5,9,14,14a-Tetrahydro-2,3-dimethoxyisoquino[1,2-b][3]benzazepin-8(6H)-one (XIIc)

A mixture of 2-[(1,2,3,4-tetrahydro-6,7-dimethoxy-1-isoqluinolyl)methyl]benzeneacetic acid methyl ester (Xc, Ex. 12) (6.8 g, 0.019 mole), sodium carbonate (2.01 g, 0.019 mole) was heated under reflux for 2 hours, then chilled in ice. A precipitate was collected on a filter and washed with water, then with methanol to give the titled product (4.8 g, 78%), mp 195°–197°.

Analysis: $C_{20}H_{21}NO_3$ Calculated: C, 74.22; H, 6.55; N, 4.33  Found: C, 74.17; H, 6.82; N, 4.37

EXAMPLE 16

2-[(1,2,3,4-Tetrahydro-6,7-dimethoxy-1-isoquinolinyl)methyl]benzeneacetic acid (XIc)

A mixture of 2-[(1,2,3,4-tetrahydro-6,7-dimethoxy-1-isoquinolinyl)methyl]benzeneacetic acid methyl ester (Xc, Ex. 12) (1.0 g, 2.8 mmole) 1.0N sodium hydroxide solution and methanol (1 ml) was heated under reflux for 1.5 hr, and filtered after being cooled to room temperature. The filtrate was acidified with dilute hydrochloric acid, and chilled in ice with scratching. A white cotton-like precipitate was collected on a filter and washed with cold water to give the titled product (0.45 g, 41%), mp 129°–145° dec.

Analysis: $C_{20}H_{23}NO_4 \cdot HCl \cdot \frac{1}{2}H_2O$ Calculated: C, 62.09; H, 6.51; N, 3.62  Found: C, 61.90; H, 6.65; N, 3.71

EXAMPLE 17

5,9,14,14a-Tetrahydro-2,3-dimethoxyisoquino[1,2-b][3]benzazepin-8(6H)-one (XIIc)

To an ice-chilled solution of 2-[(1,2,3,4-tetrahydro-6,7-dimethoxyisoquinolinyl)methyl]benzeneacetic acid (XIc, Ex. 16) (0.4 g, 1.17 mmole) and 4-dimethylaminopyridine (0.15 g, 1.23 mmol) in dry acetonitrile (45 ml) was added with stirring dicyclohexylcarbodiimide (0.24 g, 1.17 mmole). The resulting mixture was stirred at room temperature for 6 hours, then heated to boiling briefly. When the mixture was cooled to room temperature, there was separated a precipitate which was removed by filtration. The filtrate was concentrated to about 10 ml, and chilled in ice to cause a separation of a precipitate. The precipitate was collected on a filter and recrystallized from ethanol, giving the titled product (0.26 g, 69%) which is identical with that described in Example 15.

EXAMPLE 18

5,6,8,9,15,15a-Hexahydro-2,3-dimethoxy[1,3]dioxolo[4,5-h]isoquino[1,2-b][3]benzazepine (XIIIa)

To a well stirred and ice-chilled 1.0M tetrahydrofurane solution of borane-tetrahydrofurane complex was added 5,9,15,15a-tetrahydro-2,3-dimethoxy[1,3]dioxolo[4,5-h]isoquino[1,2-b][3]benzazepin-8(6H)-one (XIIa, Ex. 13) (7.0 g, 0.019 mole) suspended in tetrahydrofurane (350 ml) over a period of 20 minutes. The chilling source was removed, and the reaction mixture was heater under reflux for 1 hour. After the reaction mixture was cooled to room temperature, dilute hydrochloric acid (6.0N, 24 ml) was added slowly, and the mixture was distilled at atmospheric pressure until 340 ml of tetrahydrofurane was collected. The residue was made alkaline by dropwise addition of 50% sodium hydroxide, whereby a precipitate was separated. The mixture was chilled in ice, and the precipitate was collected on a filter and washed with ethanol to give the product (5.15 g, 77%), mp 166°–168°. The analytical sample that was obtained by recrystallization from ethanol melted at 168.170°.

Analysis: $C_{21}H_{23}NO_4$ Calculated: C, 71.37; H, 6.56; N, 3.96  Found: C, 71.48; H, 6.79; N, 3.61

EXAMPLE 19

5,6,8,9,15,15a-Hexahydro-3-methoxy-[1,3]dioxolo[4,5-h]isoquino[1,2-b][3]benzazepine (XIIIb)

The title compound was prepared as described in Example 18 by the reduction of 5,9,15,15a-tetrahydro-3-methoxy-[1,3]dioxolo[4,5-h]isoquino-[1,2-b][3]benzazepine-8(6H)-one hemiethanolate (XIIb, Ex. 14) (3.60 g, 10 mmole) with deborane in tetrahydrofurane (25 ml of 1.0M solution). The product was extracted with methylene chloride. The methylene chloride extract was dried (Na$_2$SO$_4$), and evaporated on a rotary evaporator to give an oil which solidified on standing. Recrystallization from ethanol afforded the titled compound (2.57 g, 80%), mp 133°–135°.

Analysis: $C_{28}H_{21}NO_3$ Calculated: C, 74.28; H, 6.54; N, 4.33  Found: C, 73.87; H, 6.67; N, 4.25

A portion of the product was converted into hydrochloric acid salt by treating the compound dissolved in ethanol with ethanolic hydrogen chloride, mp 239°–241° dec.

Analysis; $C_{20}H_{21}NO_3 \cdot HCl$ Calculated: C, 66.75; H, 6.16; N, 3.89  Found: C, 66.91; H, 6.13; N, 3.72

EXAMPLE 20

5,6,8,9,14,14a-Hexahydro-2,3-dimethoxyisoquino[1,2-b][3]benzazepine (XIIIc)

The title compound was prepared as described in Example 18 by the reduction of 5,9,14,14a-tetrahydro-2,3-dimthoxyisoquino[1,2-b][3]benzazepin-8(6H)-one (XIIc, Ex. 15 or 17) (3.88 g, 0.012 mole) with diborane-tetrahydrofurane comples (1.0M, 24 ml) in a 73% yield, mp 141°–143.5°, Mass. spec (CI) m/z 310 (M+H). This product was converted into hydrochloric acid salt by treating the ethanolic solution of the product with ethanolic hydrogen chloride solution, mp 222°–224° dec.

Analysis: $C_{20}H_{23}NO_2 \cdot HCl$ Calculated: C, 69.45; H, 6.99; N, 4.05  Found: C, 69.91; H, 7.23; N, 4.25

EXAMPLE 21

5,6,8,9,14,14a-Hexahydroisoquino[1,2-b][3]benzazepine-2,3-diol (XIVc)

Hydrobromic acid (48%, 30 ml) was added to a glacial acetic acid (3 ml) solution of 5,6,8,9,14,14a-hexahydro-2,3-dimethoxyisoquino[1,2-b][3]-benzazepine (XIIIc, Ex. 20) (0.928 g, 3 mmole), and the resulting solution was heated under reflux for 2.5 hours, then evaporated on a rotary evaporator to give a resinous residue. The residue was dissolved in tetrahydrofurane (about 80 ml), and the solution was allowed to sit at room temperature over a weekend. The crystalline product that was separated was collected on a filter, and washed with tetrahydrofurane to give the titled product which was recrystallized from ethanol. The product (HBr salt) weighed 0.8 g (73%) and melted at 270°–272°.

Analysis: $C_{18}H_{19}NO_2 \cdot HBr$ Calculated: C, 59.84; H, 5.58; N, 3.88 Found: C, 59.59; H, 5.56; N, 4.11

EXAMPLE 22

5,6,8,9,14,14a-Hexahydroisoquino[1,2-b][3]benzazepine-2,3,11,12-tetrol (XIVa)

Boron tribromide (1.0M solution of methylene chloride, 45 ml) was added dropwise to an ice-chilled, well stirred methylene chloride solution of 5,6,8,9,15,15a-hexahydro-2,3-methoxy[1,3]dioxolo[4,5]h]isoquino[1,2-b][3]benzazepine (XIIIa, Ex. 18) (1.77 g, 5 mmole), and the resulting mixture was stirred at room temperature overnight. Methanol (45 ml) was added dropwise to the reaction mixture, then evaporated on a rotary evaporator to give a resinous material which was dissolved in 50% aqueous methanol solution. The solution was added to a separate funnel containing 5% aqueous sodium bicarbonate solution (100 ml), and was extracted with ethyl acetate repeatedly. The combined extracts were dried (anhydrous $Na_2SO_4$), and evaporated on a rotary evaporator to afford a powdery residue. The residue was dissolved with a small amount of ethanol, and the solution was treated with ethanolic hydrogen chloride solution. Acetonitrile was added to the acidic solution until the solution became cloudy, and allowed to sit in a refrigerator overnight. The crystalline precipitate that was separated was collected on a filter and washed with acetonitrile to give the titled product (0.94 g, 55%) which was powdered with a mortar and pestle, then dried in vacuo at 78° overnight, mp 272°–276° dec.

Analysis: $C_{18}H_{19}NO_4 \cdot HCl \cdot \frac{1}{4}H_2O$ Calculated: C, 61.01; H, 5.83; N, 3.95 Found: C, 61.24; H, 5.81; N, 4.14

EXAMPLE 23

5,6,8,9,14,14a-Hexhydroisoquino[1,2-b][3]benzazepine-3,11,12-triol (XIVb)

The title compound was prepared as described in Example 22 by the treatment of 5,6,8,9,15,15a-hexahydro-3-methoxy-[1,3]dioxolo[4,5-h]isoquino[1,2-b][3]benzazepine (XIIIb, Ex. 19) (0.9 g, 2.8 mmole) with boron tribromide. The reaction time was shortened to 4 hours. Evaporation of ethyl acetate extracts on a rotary evaporator afforded a solid residue which was dissolved in hot ethanol solution with ethanolic hydrogen chloride solution. When the mixture was warmed on a steam bath with an additional amount of ethanol (15 ml), a crystalline product was separated. The mixture was chilled in a refrigerator, and the precipitate was collected on a filter and washed with ethanol to give the titled product (0.9 g, 97%). An analytical sample was obtained by dissolving the product in a mixture of ethanol and a small amount of water, and precipitation by an addition of a large amount of anhydrous ether. The product started to char at 282° and decomposed completely at 286°. Mass spec (CI) m/z 298 (M+1) and 247.

Analysis: $C_{18}H_{19}NO_3 \cdot HCl$ Calculated: C, 64.76; H, 6.04; N, 4.20 Found: C, 64.70; H, 6.21; N, 4.07

EXAMPLE 24

5,6,8,9,15,15a-Hexahydro-2,3-dimethoxy-7-methyl-[1,3]dioxolo[4,5-h]isoquino[1,2-b][3]benzazepine iodide (XIVa)

A mixture of [5,6,8,9,15,15a-hexahydro-2,3-dimethoxy]1,3]dioxolo[4,5-h]isoquino[1,2-b][3]benzazepine (XIIIa, Ex. 18) (0.71 g, 2 mmole), sodium carbonate (0.15 g, 1.5 mmole), methyl iodide (0.43 g, 3 mmole) and dimethylformamide (10 ml) was stirred at room temperature under nitrogen atmosphere for 2 days, and filtered. Addition of a large amount of anhydrous ether and chilling in ice caused separation of a precipitate which was collected on a filter. The filter residue was recrystallized from a mixture of ethanol and water to give 0.5 g (50%) of the title product, mp 258°–260°.

Analysis: $C_{22}H_{26}NO_4I$ Calculated: C, 53.34; H, 5.29; N, 2.83 Found: C, 53.41; H, 5.39; N, 2.90

What is claimed is:

1. A compound of the formula

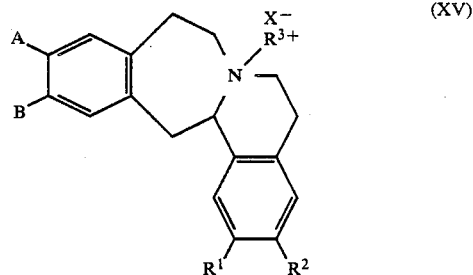

(XV)

wherein
- A and B may be, independently, hydrogen, hydroxy or $C_1$–$C_6$ alkoxy, or A and B together may be —O—$(CH_2)_n$—O— wherein n may be 1, 2 or 3;
- $R^1$ and $R^2$ may be, independently, hydrogen, hydroxy, or $C_1$–$C_6$ alkoxy;
- $R^3$ may be hydrogen or $C_1$–$C_4$ alkyl; and
- X may be a halide selected from chlorine, bromine or iodine, or $R^3$ and X may both be absent or may be replaced by other pharmaceutically acceptable cations or anions.

2. A compound of claim 1 in which one of $R^1$ and $R^2$ is hydroxy, the other is hydrogen, and A and B are both hydroxy.

3. A compound of claim 1 in which $R^1$, $R^2$, A, and B are each hydroxy.

4. A compound of claim 1 in which one of $R^1$ and $R^2$ is methoxy, the other is hydrogen, and A and B together are —O—$CH_2$—O—.

5. A compound of claim 1 in which one or both of A and B is methoxy, ethoxy or propoxy.

6. A compound of claim 1 in which one or both of $R^1$ and $R^2$ is methoxy, ethoxy or propoxy.

7. A compound of claim 1 in which $R^3$ is methyl or ethyl.

8. A compound of claim 1 in which $R^3$ is methyl and X is iodine.

9. A compound of claim 1 which is 5,6,8,9,14,14a-hexahydroisoquino[1,2-b][3]benzazepine-3,11,12-triol, hydrohalide.

10. The hydrochloride salt of the compound of claim 9.

11. A compound of claim 1 which is 5,6,8,9,15,15a-hexahydro-2,3-dimethoxy-7-methyl-[1,3-dioxolo[4,5-h]isoquino[1,2-b]benzazepinium iodide.

12. A compound of claim 1 which is 5,6,8,9,15,15a-hexahydro-3-methoxy[1,3]dioxolo[4,5-h]isoquino[1,2-b][3]benzazepine, hydrohalide.

13. The hydrochloride salt of the compound of claim 12.

14. A compound of claim 1 which is 5,6,8,9,14,14a-hexahydro-2,3-dimethoxyisoquino[1,2-b][3]benzazepine, hydrohalide.

15. The hydrochloride salt of the compound of claim 14.

16. A compound of claim 1 which is 5,6,8,9,14,14a-hexahydroisoquino[1,2-b][3]benzazepine-2,3,11,12-tetrol, hydrohalide.

17. The hydrochloride salt of the compound of claim 16.

18. A method of treating hypertension comprising administering to a mammal, including man, in need thereof an amount effective to reduce blood pressure of a compound of the formula

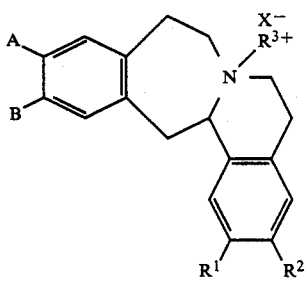

(XV)

wherein
A and B may be, independently, hydrogen, hydroxy or $C_1$-$C_6$ alkoxy, or A and B together may be —O—$(CH_2)_n$—O— wherein n may be 1, 2 or 3;
$R^1$ and $R^2$ may be, independently, hydrogen, hydroxy or $C_1$-$C_6$ alkoxy;
$R^3$ may be hydrogen or $C_1$-$C_4$ alkyl; and
X may be a halide selected from chlorine, bromine or iodine, excluding however the compounds of said formula XV in which A and B together are —O—$CH_2$—O— and $R^1$ and $R^2$ are each methoxy and in which A and B are each hydrogen and $R^1$ and $R^2$ are each hydroxy.

19. A method of claim 18 wherein the compound of formula XV is selected from a hydrohalide salt of (a) 5,6,8,9,14,14a-hexahydroisoquino[1,2-b][3]benzazepine-3,11,12-triol,
(b) 5,6,8,9,15,15a-hexahydro-3-methoxy[1,3]-dioxolo[4,5-h]isoquino[1,2-b][3]benzazepine,
(c) 5,6,8,9,14,14a-hexahydro-2,3-dimethoxyisoquino[1,2-b][3]benzazepine, or
(d) 5,6,8,9,14,14a-hexahydroisoquino[1,2-b]benzazepine-2,3,11,12-tetrol, and
(e) 5,6,8,9,15,15a-hexahydro-2,3-dimethoxy-7-methyl-[1,3]dioxolo[4,5-h]isoquino[1,2-b][3]benzazepinium halide.

20. A method of claim 19 wherein the hydrohalide salt of compounds (a)–(d) is the hydrochloride salt and the halide salt of compound (e) is the iodide salt.

21. A compound of the formula

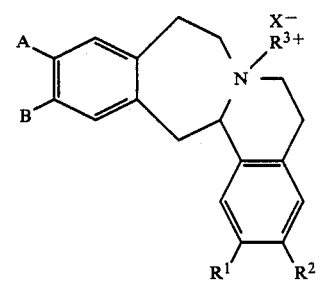

(XV)

wherein
A and B may be, independently, hydrogen, hydroxy or $C_1$-$C_3$ alkoxy, or A and B together may be —O—$(CH_2)$—O—;
$R^1$ and $R^2$ may be, independently, hydrogen, hydroxy or $C_1$-$C_3$ alkoxy;
$R^3$ may be hydrogen, methyl or ethyl; and
X may be a halide selected from chloride, bromine or iodine, or $R^3$ and X may both be absent.

22. A compound of claim 21 in which one of $R^1$ and $R^2$ is hydroxy, the other is hydrogen, and A and B are both hydroxy.

23. A compound of claim 21 in which $R^1$, $R^2$, A, and B are each hydroxy.

24. A compound of claim 21 in which one of $R^1$ and $R^2$ is methoxy, the other is hydrogen, and A and B together are —O—$CH_2$—O—.

25. A compound of claim 21 which is 5,6,8,9,14,14a-hexahydroisoquino[1,2-b][3]benzazepine-3,11,12-triol, hydrohalide.

26. The hydrochloride salt of the compound of claim 25.

27. A compound of claim 21 which is 5,6,8,9,15,15a-hexahydro-2,3-dimethoxy-7-methyl-[1,3]dioxolo[4,5-h]isoquino[1,2-b][3]benzazepinium halide.

28. The iodide salt of the compound of claim 27.

29. A compound of claim 21 which is 5,6,8,9,15,15a-hexahydro-3-methoxy[1,3]dioxolo[4,5-h]isoquino[1,2-b][3]benzazepine, hydrohalide.

30. The hydrochloride salt of the compound of claim 29.

31. A compound of claim 21 which is 5,6,8,9,14,14a-hexahydro-2,3-dimethoxyisoquino[1,2-b][3]benzazepine, hydrohalide.

32. The hydrochloride salt of the compound of claim 31.

33. A compound of claim 21 which is 5,6,8,9,14,14a-hexahydroisoquino[1,2-b][3]benzazepine-2,3,11,12-tetrol, hydrohalide.

34. The hydrochloride salt of the compounds of claim 33.

* * * * *